(12) United States Patent
Whitson et al.

(10) Patent No.: US 7,691,117 B2
(45) Date of Patent: Apr. 6, 2010

(54) LANCING DEVICE

(75) Inventors: Robert C. Whitson, Elkhart, IN (US); Norman S. Miller, Lafayette, IN (US)

(73) Assignee: Bayer HealthCare LLC, Tarrytown, NY (US)

(*) Notice: Subject to any disclaimer, the term of this patent is extended or adjusted under 35 U.S.C. 154(b) by 725 days.

(21) Appl. No.: 11/487,795

(22) Filed: Jul. 17, 2006

(65) Prior Publication Data

US 2006/0259060 A1    Nov. 16, 2006

Related U.S. Application Data

(63) Continuation of application No. 10/685,073, filed on Oct. 14, 2003, now Pat. No. 7,144,404.

(60) Provisional application No. 60/418,422, filed on Oct. 15, 2002.

(51) Int. Cl.
*A61B 17/34* (2006.01)

(52) U.S. Cl. .................. 606/182; 606/181; 606/184

(58) Field of Classification Search ................ 606/181, 606/184
See application file for complete search history.

(56) References Cited

U.S. PATENT DOCUMENTS

| 5,196,025 | A | 3/1993 | Ranalletta et al. |
| 5,267,963 | A | 12/1993 | Bachynsky |
| 5,304,193 | A * | 4/1994 | Zhadanov .................. 606/182 |
| 5,318,583 | A | 6/1994 | Rebenau et al. |
| 5,527,334 | A | 6/1996 | Kanner et al. |
| 5,628,764 | A | 5/1997 | Schraga |
| 5,938,679 | A | 8/1999 | Freeman et al. |
| 5,997,561 | A | 12/1999 | Bocker et al. |
| 6,022,366 | A | 2/2000 | Schraga |
| 6,152,942 | A | 11/2000 | Brenneman et al. |
| 6,231,531 | B1 | 5/2001 | Lum et al. |
| 6,409,740 | B1 * | 6/2002 | Kuhr et al. .................. 606/182 |
| 6,858,015 | B2 | 2/2005 | List |

FOREIGN PATENT DOCUMENTS

EP    1 254 632 A1    4/2002

OTHER PUBLICATIONS

European Search Report for European Patent Application Number EP 03 02 2296, dated Jan. 30, 2004 (1 page).

* cited by examiner

*Primary Examiner*—Corrine M McDermott
*Assistant Examiner*—Christopher D Prone
(74) *Attorney, Agent, or Firm*—Nixon Peabody LLP

(57) ABSTRACT

A lancing device comprising a movable parallelogram-shaped rack. The rack rotates a linearly fixed pinion which drives a slider-crank system. The slider-crank system in turn drives a lance holder. The parallelogram-shaped rack defines one or more predetermined paths along which the pinion moves. The lance holder is prevented from being extended beyond a predetermined depth when the pinion reaches a predetermined position along the one or more predetermined paths. The pinion is mechanically stopped from further progress by intersecting two legs of the parallelogram-shaped rack. Teeth of the rack may be modified to reduce the change the pinion may jam in the rack.

19 Claims, 6 Drawing Sheets

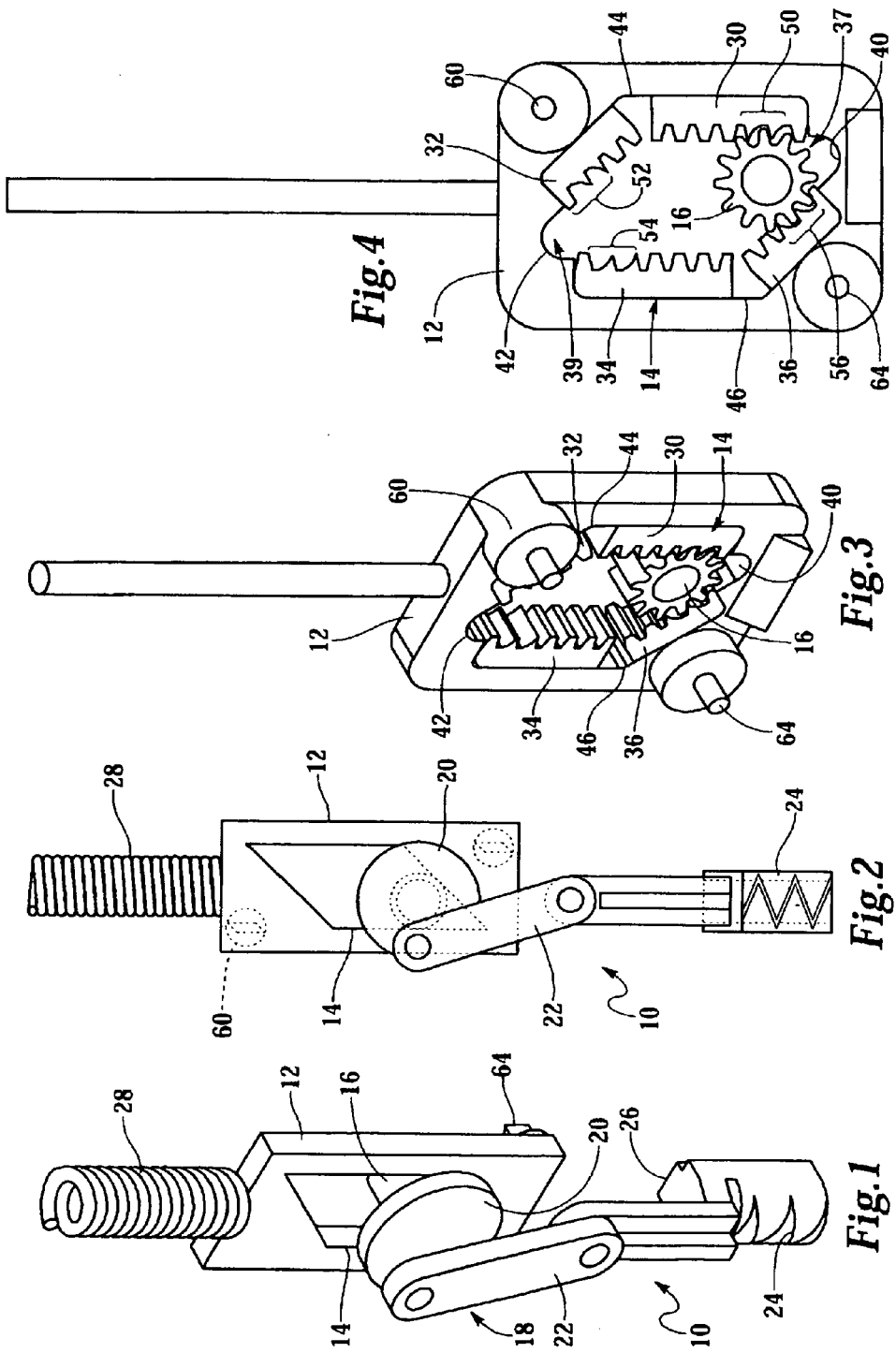

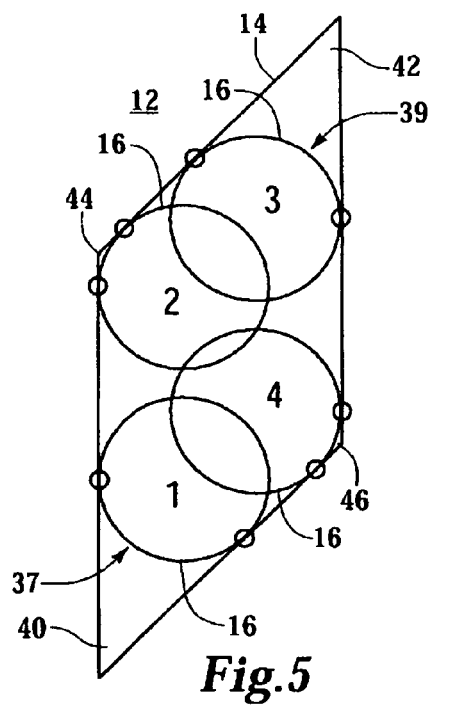
Fig.5
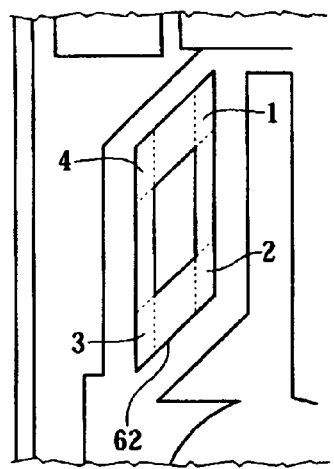
Fig.6
| PINION POSITION | 1 | 2 | 3 | 4 |
|---|---|---|---|---|
| SLIDER CRANK POSITION | | | | |
Fig.7

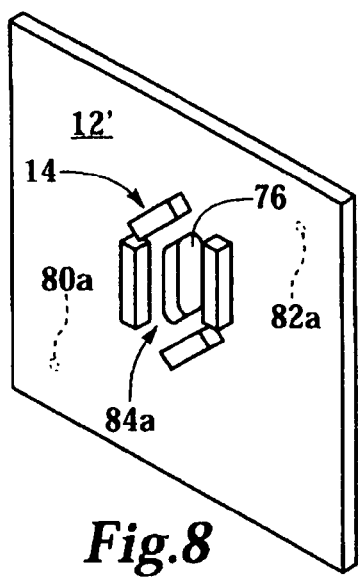
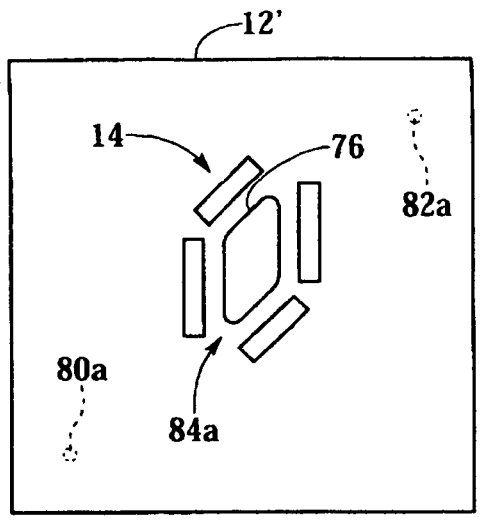
*Fig.8*  *Fig.9*
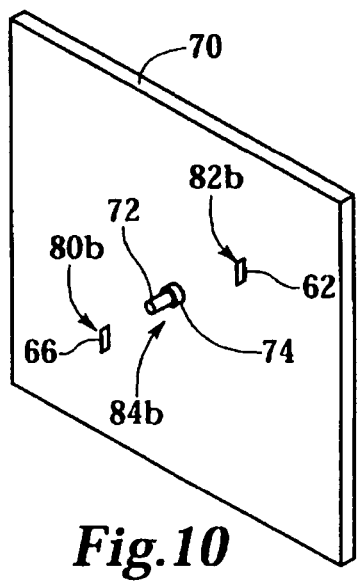
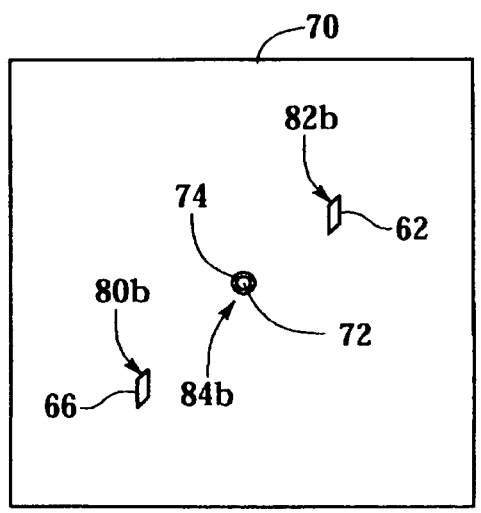
*Fig.10*  *Fig.11*
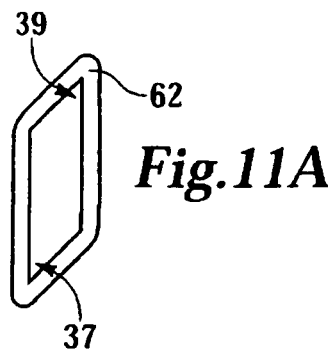
*Fig.11A*

LANCING DEVICE

CROSS-REFERENCE TO RELATED APPLICATIONS

This application is a continuation of application Ser. No. 10/685,073, filed on Oct. 14, 2003, now U.S. Pat. No. 7,144,404 which claims the benefit of U.S. Provisional Application 60/418,422, filed on Oct. 15, 2002, in which both applications are hereby incorporated by reference in its entirety.

FIELD OF THE INVENTION

The present invention relates generally to blood monitoring devices, and more particularly, to a lancing mechanism, or lancing device, for lancing a patient's skin to obtain a sample of blood for analysis.

FIELD OF THE INVENTION

The present invention relates generally to blood monitoring devices, and more particularly, to a lancing mechanism, or lancing device, for lancing a patient's skin to obtain a sample of blood for analysis.

BACKGROUND OF THE INVENTION

It is often necessary to, quickly obtain a sample of blood and perform an analysis of the blood sample. Preferably obtaining the blood is as painless as possible. One example in which there is a need for painlessly obtaining a sample of blood is in connection with a blood glucose monitoring system where a user must frequently use the system to monitor the user's blood glucose level.

One method of monitoring a person's blood glucose level is by portable hand-held blood glucose testing device. The portable nature of these devices enables the user to conveniently test his blood glucose levels wherever the user may be. To check the blood glucose level, a drop of blood is obtained from him, for example, from the fingertip using a separate lancing device. The lancing device contains a lance or lancet to puncture the skin. Once the requisite amount of blood is produced on the fingertip, the blood is harvested using the blood glucose-testing device. The blood is drawn inside the testing device, which then determines the concentration of glucose in the blood. The results of the test are communicated to the user by a display on the testing device.

Many prior art lancing devices use a spring directly coupled to the lance to move the lance to its penetration depth. The lance is drawn back to compress the spring. When released, the spring extends, thus forwardly propelling the lance to its penetration depth. More detail concerning lancing devices is set forth in U.S. Pat. No. 6,152,942, which is commonly assigned and incorporated herein by reference in its entirety. One problem associated with other prior lancing devices is that the penetration depth of the lance is dependent on a spring constant, which is a measure of the spring stiffness. The mechanical quality of the spring, including the stiffness, tend to vary, and in particular degrade, over time with use. Accordingly, over time, the penetration depth of prior art lances may vary. When the penetration depth of the lance lessens over time, the lance may not produce a laceration deep enough to draw the requisite volume of blood necessary for blood glucose analysis. Insufficient lancing can result in erroneous analysis if the user does not recognize that the lancing has not produced the requisite volume of blood for analysis. And if the user does recognize an insufficient lancing has incurred the user must re-lance resulting in another laceration in the user's skin and more pain. The user may eventually have to replace the lance, or the entire device because the accuracy and consistency of the laceration has degraded.

Another related problem associated with many prior art lancing devices is that when the spring forwardly advances the lance to its penetration depth, the spring extends past its static length. The spring then retracts the lance. But due to the oscillary nature of the spring, the lance is retracted past its static retraction position. If the lance continues to oscillate in this manner, it may repeatedly enter the laceration and penetrate the user's skin several times. With each actuation of such an oscillating lance, the user's skin is lanced several times which results in a larger laceration. A larger laceration in the user's skin translates into more pain for the user and a longer time for the laceration to heal.

Other problems associated with prior art lancing device include vibration and chatter of the lance during the lancing process. The vibration and chatter result in uncontrolled movement of the lance. Such uncontrolled movement may result in larger as well as more jagged lacerations. Another detrimental result is inaccurate punctures in the skin, with respect to both location and depth of the puncture.

Accordingly there is a need for continued improvement in lancing devices and glucose monitoring systems generally.

SUMMARY OF THE INVENTION

A lancing device according to the invention comprises a movable parallelogram-shaped rack. The rack rotates a linearly fixed pinion. The pinion drives a slider-crank system that comprises a drive wheel and a drive arm. The terms lance and lancet are used interchangeably herein. The drive arm in turn moves a lance holder which is supported to move in a linear path of motion. The pinion may be integral with the drive wheel, wherein the drive arm is connected directly to the pinion.

The parallelogram-shaped rack comprises a pair of acute angles and a pair of oblique angles. In the illustrated embodiment, the acute angle, which is furthest from the lance, but closest to the spring is referred to as the proximal acute angle and the other angle (located furthest from the spring) is referred to herein as the distal acute angle.

When the rack is in a cocked position the pinion is positioned proximate to the distal acute angle and a spring is compressed to apply a force in the direction of extending the lance. Upon releasing the rack, with a fulcrum or trigger, for example, the spring forces the rack downward such that the pinion rotates along as a first rack segment of the rack and then intersects the first oblique angle. The pinion then follows a second rack segment to the proximal acute angle.

The pinion being positioned at the proximal acute angle is also referred to herein as the fired position of the rack, or simply the fired position. For some applications, the oblique angles are 45 degrees; other angles will be determined according to the particular applications. In particular applications, the pinion rotates 180 degrees as it travels along the first and second rack segment from a cocked position to the fired position. The cocked position corresponds to the pinion being at the distal acute angle. Pulling the rack back in the opposite direction by a cocking force moves the pinion along third and fourth rack segments from the fired position to the cocked position.

A modified rack allows for a complete 360 degree rotation of the pinion as the rack moves through one cycle, e.g., from a cocked position to a fired position and back to a cocked position, without jamming the pinion. For many applications it is desirable that the rack is always in contact with the pinion, thus the exact position of the pinion relative to the rack may be determined. The rack is modified at both acute angles to reduce the possibility of the pinion becoming jammed in either of the acute angles. In one embodiment at least two teeth on each rack segment, for example, the two teeth on each segment positioned closest to each acute angle, are modified to create wider gaps between teeth. In the particular illustrated embodiment, both gap walls (the tooth portion that forms the gap) of each of the two teeth further from the acute angle corners are opened wider, while the gap walls closer to the corners of the acute angle are maintained in their conventional shape.

A guide pin and guide track combination may be used to guide the rack relative to a fixed plate. The term "plate" is used to generally refer to any relatively fixed structure. For example, the web of a housing of a portable lance may be referred to as a plate, in this context. The guide pin may be located, e.g., in a fixed position relative to the rack while the guide track is located in a fixed position on the fixed plate. For some applications, the guide track is a parallelogram and the pin is a parallelogram. Other pin and track combinations and shapes will be apparent to those of ordinary skill in the art. For example, the pin may be a typical cylindrical protrusion from a frame supporting the parallelogram-shaped rack. Alternatively, the pin may extend from the plate, for example.

The invention overcomes problems associated with the prior art and satisfies a variety of objectives.

OBJECT OF THE INVENTION

An object of the invention is to provide an improved glucose-monitoring device.

Another object of the invention is to provide an improved lancing device.

Another object is to precisely control depth penetration and puncture location of a lance.

Another object is to prevent multiple inadvertent punctures.

Another object is to reduce lance vibration and chatter.

Another object is to provide a lance that repeatedly penetrates to a consistent depth over the lifetime of an apparatus used to force the lance into an extended position. An apparatus providing such force may, for example, be a replaceable spring. In such an application, an object is to maintain consistency of operation throughout the life of the lance device, rather than a portion of the life of one spring.

Another object is to mechanically prevent more than one puncture from occurring.

Another object is to provide a compact hand-held lancing device that is easy to operate. A further object is to encase the lancing device in casings contoured to facilitate gripping the device. Another object is to provide the lancing device with external means for ensuring a consistent perpendicular lancing operation, where such means may, for example, comprise an end cap having a face perpendicular to the lancing motion.

Another object is to provide the lancing device with a flush mounted trigger or other means to reduce protruding parts that may potentially jab a user or break off. Another object is to provide a lancing device that is not prone to chattering and auto-jarring motions during the lancing operation. A further object is to provide a lancing device a reduced number of external moving pieces, such as handles, during the lancing operation.

Another object is to provide a durable, yet inexpensive, lancing device that provides consistent lance punctures over the life of one or more springs, wherein the springs may be easily replace by opening the device.

Other objects and advantages will be apparent to those of skill in the art from the teachings herein.

BRIEF DESCRIPTION OF THE DRAWINGS

FIG. 1 shows a perspective view of a lancing device.

FIG. 2 shows a side elevation view of the lancing device shown in FIG. 1.

FIG. 3 shows an enlarged view corresponding to FIG. 1; looking from the reverse side.

FIG. 4 shows an enlarged view corresponding to FIG. 2; looking from the reverse side.

FIG. 5 shows representative positions of the pinion as it moves along the rack shown in FIG. 2.

FIG. 6 shows corresponding positions of a guiding pin in a guiding track. The positions correspond to the pinion positions represented in FIG. 5.

FIG. 7 shows representative slider-crank positions corresponding to the pinion positions represented in FIG. 5.

FIG. 8 shows a frame comprising a cut-out for interfacing with the pinion axle.

FIG. 9 shows a front view of the frame shown in FIG. 8.

FIG. 10 shows a plate for interfacing with the frame shown in FIG. 8.

FIG. 11 shows a front view of the plate shown in FIG. 10.

FIG. 11A shows an enlarged view of the guide track shown in FIG. 11.

DESCRIPTION OF ILLUSTRATIVE EMBODIMENTS

Figure 12:
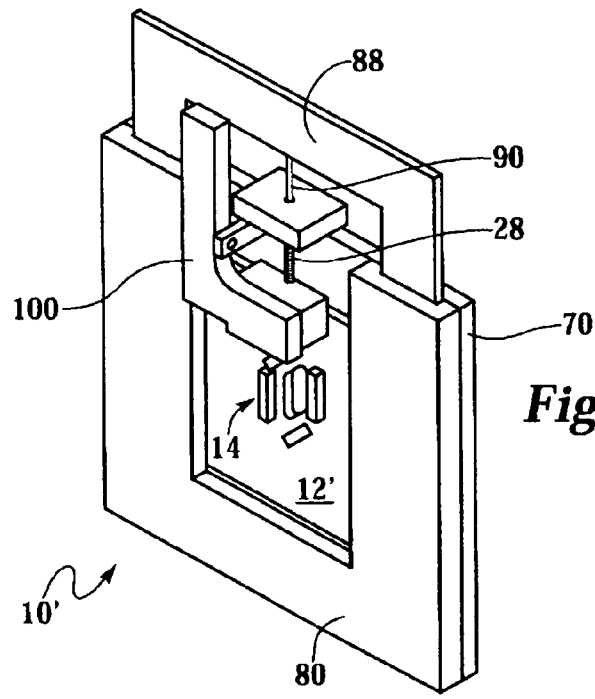
FIG. 12 shows a lancing device comprising the plate and frame shown in FIGS. 8 and 10.

FIG. 1 shows a lancing device 10, in perspective view, for use with a lance (not shown). The device 10 comprises a frame 12 supporting a parallelogram-shaped rack 14. The rack 14 is better seen in FIG. 2 which is a side elevation view of the lancing device 10. FIGS. 3 and 4 show the reverse side of the frame 12 shown in FIGS. 1 and 2. A pinion 16 is rotatably supported in the rack 14. Rotation of the pinion 16 is coupled to movement of the rack 14. A slider-crank system 18 is coupled to the pinion 16 and comprises a drive wheel 20 and drive arm 22 coupled to a lance holder 24. The drive wheel 20 may be integral with the pinion 16. The lance holder 24 may comprise a rail 26 to interface with a slot (not shown); the lance holder 24 moves linearly in the slot in response to rotation of the pinion 16.

A drive spring 28 applies force to the frame 12 for moving the rack 14, wherein the pinion 16 is rotated counterclockwise (clockwise in FIGS. 3 and 4) and the slider-crank system 18 moves the lance holder 24 from a retracted position to an extended position. Further rotation moves the lancet holder 24 from the extended position to the retracted position. It will be understood by those of ordinary skill in the art that where the lancing device is embodied in a housing, extension and retraction of the lance holder does not require the lance holder to be extended from the housing or retracted into the housing. But when the lance holder is in the retracted position a lance is typically within the housing, and when the lance holder is in the extended position, the lance is typically extended beyond the housing.

FIGS. 3 and 4 show perspective and side elevation views of the frame 12 (reversed from the view shown in FIGS. 1 and 2), which comprises first, second, third and fourth rack segments 30, 32, 34 and 36. The first and second rack segments 30 and 32 form a path, along which the pinion 16 moves from a cocked position 37 to a fired position 39. In the illustrated embodiment, the pinion 16 is linearly fixed and the frame 12 is movable relative to the pinion 16. Accordingly, movement of the pinion 16 from the cocked position 37 to the fired position 39 is equivalent to moving the frame 12 from the cocked position 37 to the fired position 39. As the frame 12 moves from the cocked position 37 to the fired position 39, the pinion 16 rotates counterclockwise (clockwise in FIGS. 3 and 4) along a predetermined fire path defined by the first and second rack segment 30, 32 until the pinion 16 is mechanically stopped at the fired position 39, whereupon the pinion 16 is simultaneously in contact with the second rack segment 32 and the third rack segment 34. The third and fourth rack segment 34 and 36 define a cocking path between the fired position 39 and the cocked position 37.

The fourth and first rack segments 36 and 30 form a distal acute angle 40. Similarly, the second and third rack segments 32 and 34 form a proximal acute angle 42. When the pinion 16 is located at the proximal acute angle 42, the device 10, and the lance holder 24 in particular, is in the fired position 39. Likewise, pinion 16 located at distal acute angle 44 corresponds to the cocked position 37. The fire path comprises a fire-path oblique angle 44. Similarly, the cocking path comprises a cocking-path oblique angle 46.

The frame 12 is moved into the cocked position 37 by any of known conventional methods, such as a pull handle, and is held in the cocked position by an arm or trigger supported by a fulcrum, for example. To reduce the chance that the pinion 16 will be jammed in the rack 14 a plurality of teeth of the rack segments are modified by widening gaps between teeth. In the illustrated embodiment shown in FIG. 4, each rack segment comprises at least two modified teeth 50, 52, 54 and 56, respectively. The pairs of modified teeth are positioned close to the acute angles. The modified teeth are shaped so the gaps between teeth are enlarged towards the opposing acute angle, i.e., toward the interior of the parallelogram. Thus, each segment comprises a plurality of modified teeth proximate the acute angle from which the segment extends.

The lancing device 10 may be provided with guide means for guiding the rack 14 as it moves between cocked position 37 and fired position 39. With reference to FIGS. 1-4, the frame comprises a guide pin 60 fixed relative to the parallelogram-shaped rack 14. The guide pin 60 interfaces a guide track 62, such as for example shown in FIGS. 6 and 11A, wherein the guide pin 60 follows the guide track 62 as the frame 12 moves between positions. A second guide pin 64 may be fixably positioned relative to the guide pin 60, wherein the parallelogram-shaped rack 14 is positioned between the guide pin 60 and the second guide pin 64. The second guide pin 64 similarly interfaces a second guide track 66. The guide tracks 62 and 66 are linearly fixed relative to the pinion 16.

FIGS. 5, 6 and 7 show relative positions of the pinion 16 and pin 60 as the frame 12 moves from cocked position 37 to fired position 39. Pinion 16 positions are designated by circles 1-4 in FIG. 5. FIG. 6 denotes the location of guide pin 60 relative to guide track 62 wherein the identified positions (1-4) correspond to the pinion positions (1-4) identified in FIG. 5. FIG. 7 denotes slider-crank positions corresponding to the pinion positions depicted in FIG. 5. The pinion 16 is in position 1 when the frame 12 is in the cocked position 37. As the frame 12 is released, the spring 28 drives the frame 12 downward and the pinion 16 rotates counterclockwise to position 2, at the fire-path oblique angle 44. As the spring 28 continues to force the frame 12 downward, the pinion 16 continues upward and to the right to position 3, at the proximal acute angle 42. The pinion 16 is mechanically stopped by interfacing with the second and third rack segments 32 and 34. As the frame 12 is pulled into the cocked position 37, the pinion 16 continues to rotate counterclockwise, moving from position 3 to position 4 and to position 1.

For some applications, the guide track 62 is preferably a parallelogram. Furthermore, the pin 60 may be parallelogram shaped to further stabilize the frame 12 due pin 60 interfacing more completely with the guide track 62, e.g., walls of the pin slide along walls of the track, thereby allowing only relative translation while preventing rotation between the pin 60 and the track 62. Depending on the application, the pinion 16 rotates 180 degrees as the pinion 16 moves from the cocked position 37 to the fired position 39 and another 180 degrees in the same direction of rotation (counterclockwise) as the pinion 16 moves from the fired position 39 to the cocked position 37. The pinion pitch diameter is, for some applications, approximately 0.25 inches.

FIGS. 8-11A show embodiments of frame 12' and a plate 70, wherein the guide means for guiding the frame 12' relative to the plate 70 comprises additional guiding means. For clarity of describing concepts of the invention, similar numbering is used to reference similar structure. The plate 70 comprises a pinion axle 72 normal to a plane parallel the plate 70, e.g., extending perpendicular from the plate 70. The pinion 16 is rotatably supported on the pinion axle 72, whereby the pinion 16 is linearly fixed relative to the plate 70. The pinion axle 72 comprises an enlarged hub 74. The frame 12' comprises a parallelogram shaped cut-out 76 generally conforming to the parallelogram-shaped rack 14. The enlarged hub 74 and parallelogram-shaped cut-out 76 are adapted to interface when the frame 12' is positioned relative to the plate 70 such that the pinion 16, which is rotatably mounted on the pinion axle 72, interfaces with the rack 14. When pinion 16 rotates along the rack 14, the enlarged hub 74 moves along the cut-out 76. With addition of the pinion and rack interface, first, second and third interfaces, namely 80, 82 and 84 provide guiding means. The interfaces 80, 82 and 84, respectively, comprise the interfaces formed between the guide pin 60 and the guide track 62, the guide pin 64 and the guide track 66, the enlarged hub 74 and the parallelogram-shaped cut-out 76. The interfaces act to stabilize movement of the frame relative to the plate. But not all three interfaces are required to provide guide means; one is sufficient.

Figure 13:
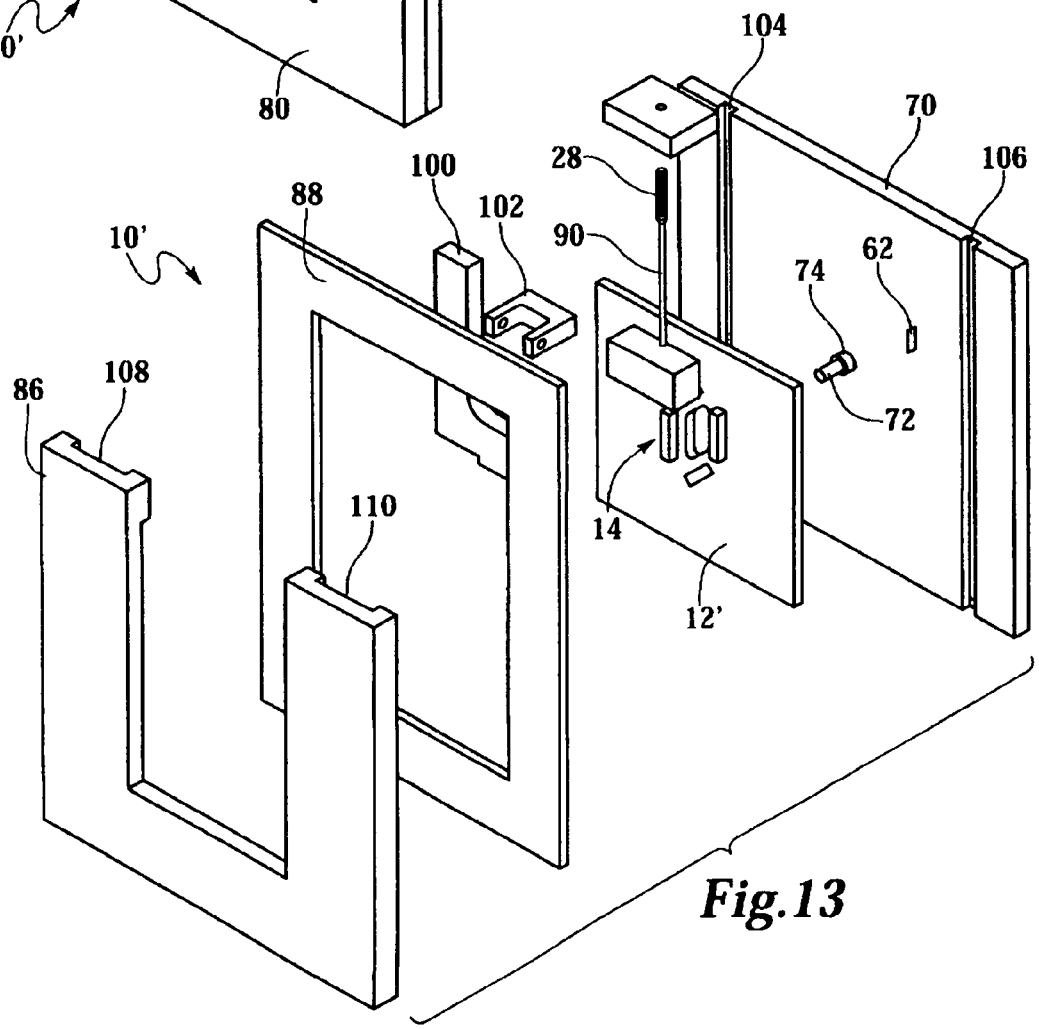
FIG. 13 shows an exploded view of the device shown in FIG. 12.

FIGS. 12 and 13 show a lancing device 10' wherein the frame 12' is mounted for translation between plate 70 and top plate 86. Pull handle 88 is used to pull the frame 12' upward and compress spring 28 until spring guide 90 is secured by release arm 100. Release arm 100 is pivotally supported by fulcrum 102. Pull handle 88 comprises protruding members (not shown) that interface with slots 104 and 106 of plate 70 to allow frame 12' to be flush mounted in pull handle 88. The pull handle 88 is flush mounted with the top plate 86, which includes guides 108 and 110 to further stabilize the components relative to each other. The components are placed in conforming relation to reduce unwanted rotation while allowing translation.

From the foregoing it is apparent that a method in accordance with the invention comprises creating a laceration with a lance. One such method comprises moving a pinion 16 along a predetermined path (30 and 32) which comprises an oblique angle 44. A lance is constrained to move in a linear motion immediately prior to reaching an extended position. Movement of the pinion 16 is coupled to a lance holder 24 such that the lance holder 24 is extended when the pinion 16 reaches a predetermined position 39 on the predetermined path (30 and 32).

Linear motion of the lance as used above, refers to direction (e.g., translation) rather than velocity or acceleration of the lance. Accordingly, although the speed of the lance holder may vary over the life of the spring 28, it is intended that the spring 28, or other conventional force means, move the lance holder 24 to a predetermined depth that does not vary over the life of the spring. Extension of the lance holder 24 beyond the predetermined depth is prevented in the illustrated embodiment because movement of the pinion 16 in further a proximal direction (upward in FIGS. 2 and 5) relative to the frame 12 it prevented when the pinion 16 interfaces with the second and third rack segment 32 and 34.

By way of example, another method of lancing comprises moving the pinion 16 along the predetermined path (30 and 32) and stopping movement of the pinion 16 at a predetermined position 39 on the predetermined path. Movement of a lance is coupled to movement of the pinion 16. The method further comprises preventing the lance holder 24 from extending beyond a predetermined depth, wherein the lance holder 24 is at the predetermined depth when the pinion 16 is at the predetermined position. For example, the lance holder 24 is in the extended position when the pinion 16 reaches the fired position 39. The lance is thereby consistently extended to the same depth over the life of one or more springs.

Figure 14:
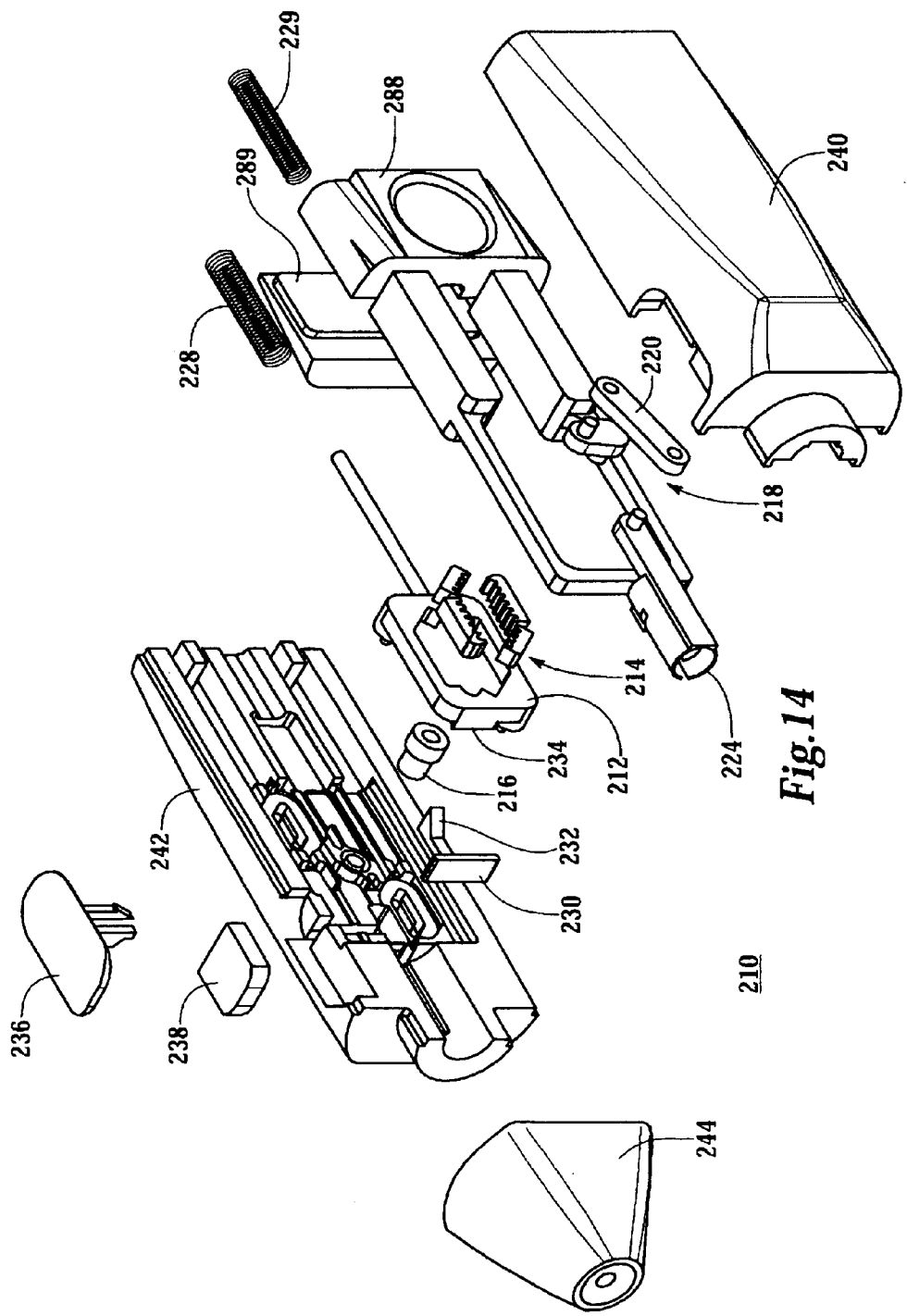
FIG. 14 shows an expanded view of a lancing device.

FIG. 14 depicts an expanded perspective view of a lancing device 210 which comprises a frame 212 supporting a parallelogram-shaped rack 214. Pinion 216 is positioned to interact with rack 214 such that frame 212 moves in a predefined path. Slider-crank system 218, comprising drive arm 220, couples movement of rack 214 to a lance holder 224. Lance holder 224 is moved into a cocked position by pulling on upper pull handle 288, which is affixed to lance holder 224, and lower 289 pull handled, which is snap fitted to upper pull handle 288. Drive spring 228 is thereby compressed and stores energy needed for driving the rack 214 forward. Return spring 229, which is positioned in a channel in the upper pull handle 288, acts to return the pull handles to the cocked position after the handles have been pulled past the point where a rack release 230 locks frame 212 in the cocked position. Thus, the drive spring 228 is maintained in a compressed state because the rack release 230 prevents the frame 212 from sliding forward, until the release is triggered. By returning the pull handles 288 and 289 to their rest position with the return spring 229, the handles are prevented from inadvertently catching a finger or thumb when the lance is extended by driving the frame 212 forward. Another concern with allowing the frame 212 to drive the pull handles is that the puncture would may be affected by the handles slamming into the casing.

The rack release 230 comprises an extension 232 that depresses as it slides over a conforming extension 234 integral with frame 212. The illustrated extensions are relatively small ramps. Depressing release button 236 disengages the rack release 230 by pushing the extension (rack-release ramp) away from frame ramp 234, thereby firing the lance. Release button 236 is returned to a set position by release button foam spring 238.

Frame 212 and lance holder 224 are operatively positioned in upper case 240 and lower case 242. The cases are snap-fitted together, or maintained together by other conventional means. End cap 244 is removable and protects a disposable lance (not shown). The end cap 244 also helps ensure proper lancing depth. The end cap has a face perpendicular to the lancing motion. The user can thereby stabilize the lancing device by placing the end cap face flush against the skin to ensure a perpendicular lancing operation.

Figure 15:
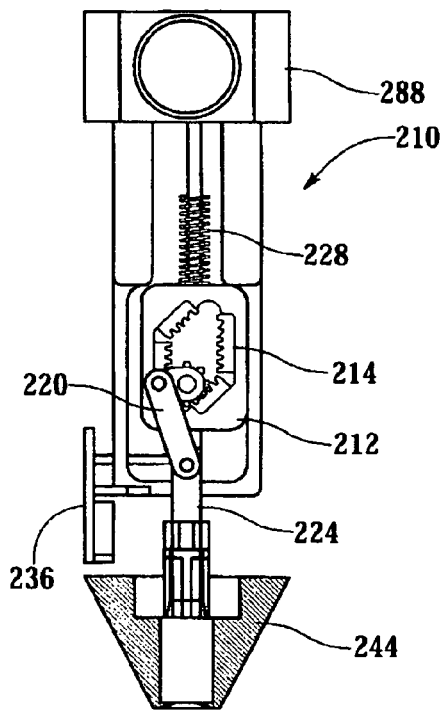
FIG. 15 shows a side elevation view of the lancing device shown in FIG. 14 with the upper and lower casings removed.
Figure 16:
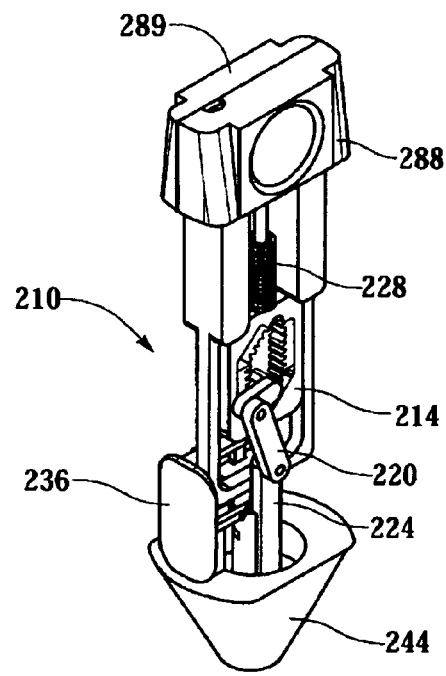
FIG. 16 shows a rotated perspective view of the lancing device shown in FIG. 15.
Figure 17:
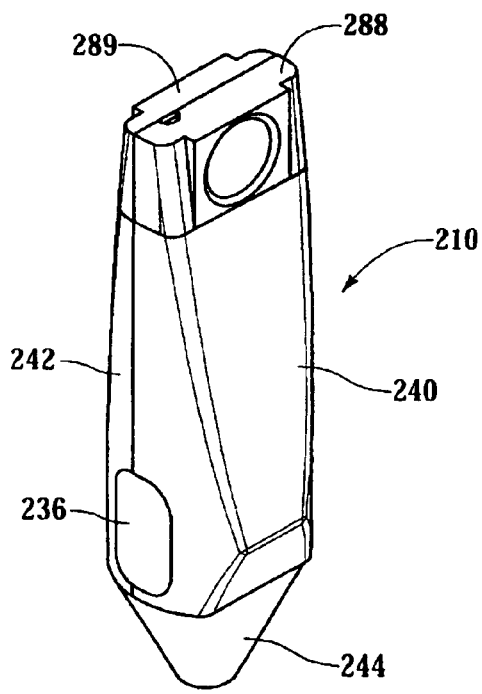
FIG. 17 shows the lancing device shown in FIG. 16 with the casings in place.
Figure 18:
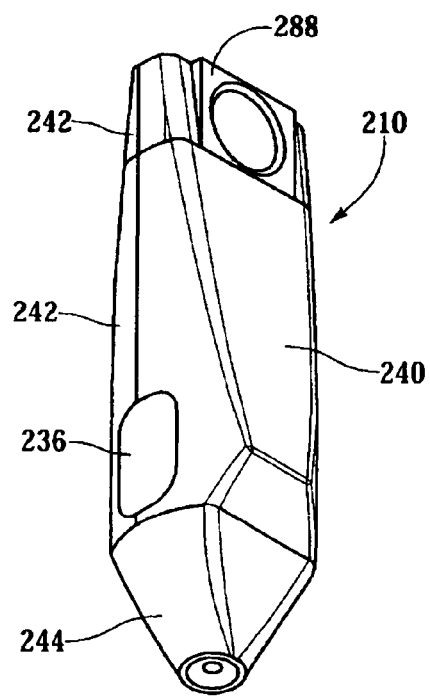
FIG. 18 shows the lancing device of FIG. 17 rotated to show the end cap.

FIG. 15 shows a side elevation view of lancing device 210 with upper and lower cases 240 and 242 removed. FIG. 16 shows an assembled view of lancing device 210 without upper case 240 and lower case 242. FIG. 17 and 18 show assembled perspective views of lancing device 210.

Alternative Embodiment A

A lancing device for use with a lance, the device comprising:
 a parallelogram-shaped rack;
 a pinion rotatably supported in the rack, wherein rotation of the pinion is coupled to movement of the rack;
 a slider-crank system comprising a drive arm coupled to the pinion; and
 a lance holder coupled to the drive arm, wherein rotation of the pinion drives the lance holder in linear motion.

Alternative Embodiment B

The device of Alternative Embodiment A comprising a drive wheel coupling the drive arm to the pinion.

Alternative Embodiment C

The device of Alternative Embodiment A wherein:
 the parallelogram-shaped rack comprises a proximal acute angle, and a distal acute angle positioned closer to the lance holder than the proximal acute angle; and
 the pinion rotates 180° when moving between the distal acute angle and the proximal acute angle.

Alternative Embodiment D

The device of Alternative Embodiment C wherein the lance holder moves from a cocked position to a fired position and wherein the lance holder is in the cocked position when the pinion is positioned at the distal acute angle and in the fired position when the pinion is positioned at the proximal acute angle.

Alternative Embodiment E

The device of Alternative Embodiment C comprising:
 a first guide pin fixed relative to the parallelogram-shaped rack; and
 a first guide track linearly fixed relative to the pinion, wherein the first guide pin movable interfaces with the first guide track as the parallelogram-shaped rack moves relative to the pinion, whereby movement of the rack is guided.

Alternative Embodiment F

The device of Alternative Embodiment E comprising:
a second guide pin fixed relative to the parallelogram-shaped rack, wherein the rack is positioned between the first and second guide pins; and
a second guide track fixed relative to the first guide track, wherein the pinion is positioned between the first and second guide tracks and the second guide pin movable interfaces with the second guide track as the parallelogram-shaped rack moves relative to the pinion.

Alternative Embodiment G

The device of Alternative Embodiment F wherein the first and second guide tracks are parallelogram shaped.

Alternative Embodiment H

The device of Alternative Embodiment E wherein the first guide track is parallelogram shaped.

Alternative Embodiment I

The device of Alternative Embodiment H wherein the first guide pin is parallelogram shaped.

Alternative Embodiment J

The device of Alternative Embodiment A comprising a drive spring positioned to move the lance holder.

Alternative Embodiment K

The device of Alternative Embodiment J wherein the parallelogram-shaped rack is positioned between the lance holder and the drive spring.

Alternative Embodiment L

The device of Alternative Embodiment A wherein:
the rack comprises four segments;
the pinion moves between a first acute angle position and a second acute angle position;
the pinion comprises teeth;
the rack segments comprise teeth adapted to engage the pinion teeth; and
at least two teeth on each segment are modified to reduce chances of the pinion jamming at either one of the first and second acute angle positions.

Alternative Embodiment M

The device of Alternative Embodiment A wherein the pinion rotates 360° as the lance holder linearly moves from a cocked position to a fired position and back to the cocked position.

Alternative Embodiment N

A lancing device for use with a lance, the device comprising:
a frame comprising a parallelogram-shape rack, wherein the frame is movably supported;
a pinion rotatably mounted to interface the rack, wherein rotation of the pinion is coupled to movement of the rack; and
a lance holder movable between a fired position and a cocked position, wherein movement of the lance holder is in response to rotation of the pinion.

Alternative Embodiment O

The device of Alternative Embodiment N wherein the lance holder moves from the cocked position to the fired position as the pinion rotates 180°.

Alternative Embodiment P

The device of Alternative Embodiment O wherein the pinion traverses approximately one-half of the rack as the lance holder moves from the cocked position to the fired position.

Alternative Embodiment Q

The device of Alternative Embodiment N wherein the parallelogram-shaped rack comprises a first acute angle and a second acute angle and the pinion is positioned proximate to the first acute angle when the lance holder is in the cocked position and the pinion is positioned proximate to the second acute angle when the lance holder is in the fired position.

Alternative Embodiment R

The device of Alternative Embodiment Q wherein the pinion rotates 180° as the pinion moves from the first acute angle to the second acute angle.

Alternative Embodiment S

A lancing device for use with a lance, the device comprising:
a plate;
a pinion linearly fixed relative to the plate;
a frame movable relative to the plate and comprising two rack segments positioned to form an oblique angle between the two rack segments, wherein the frame is movable between a cocked position and a fired position and the pinion is positioned to travel along the two rack segments as the frame moves from the cocked position to the fired position; and
a lance holder coupled to movement of the pinion, wherein the lance holder is linearly movable from a retracted position to an extended position as the frame moves from the cocked position to the fired position.

Alternative Embodiment T

The device of Alternative Embodiment S comprising a spring positioned to move the frame from the cocked position to the fired position.

Alternative Embodiment U

The device of Alternative Embodiment S comprising a slider-crank system coupling movement of the pinion to the lance holder, wherein moving the frame moves the lance holder.

Alternative Embodiment V

The device of Alternative Embodiment U wherein the slider-crank system comprises a drive arm connecting the pinion and the lance holder.

Alternative Embodiment W

The device of Alternative Embodiment V wherein the pinion rotates 180° as the frame moves from the cocked position to the fired position.

Alternative Embodiment X

The device of Alternative Embodiment S comprising guide means for guiding movement of the frame relative to the plate.

Alternative Embodiment Y

The device of Alternative Embodiment S comprising slider-crank means for coupling movement of the pinion to the lance holder, wherein moving the frame moves the lance holder.

Alternative Embodiment Z

A lancing device for use with a lance, the device comprising:
- a frame;
- rack and pinion means for moving the frame along a predetermined path from a cocked position to a fired position, wherein the rack and pinion means comprises one or more rack segments fixed relative to the frame, and a pinion interfacing the one or more rack segments;
- lance holder means for holding and moving the lance in linear motion from a retracted position to a predetermined extended position;
- means for coupling movement of the frame to the lance holder means such that the lance holder moves the lance from the retracted position to the extended position as the frame moves from the cocked position to the fired position along the predetermined path; and
- means for preventing the lance from extending beyond the predetermined extended position.

Alternative Embodiment AA

The device of Alternative Embodiment Z comprising guide means for guiding the frame along the predetermined path.

Alternative Embodiment BB

The device of Alternative Embodiment Z comprising spring means for moving the frame from the cocked position to the fired position.

Alternative Embodiment CC

The device of Alternative Embodiment BB comprising release means for releasing the frame from the cocked position and allowing the spring means to move the frame to the fired position.

Alternative Embodiment DD

The device of Alternative Embodiment CC wherein the one or more rack segments form a parallelogram.

Alternative Embodiment EE

The device of Alternative Embodiment Z wherein the one or more rack segments form a parallelogram.

Alternative Embodiment FF

The device of Alternative Embodiment Z wherein the predetermined path along which the frame moves is non-linear.

Alternative Process GG

A method of creating a laceration with a lance, the method comprising:
- moving a pinion along a predetermined path comprising an oblique angle;
- constraining a lance holder to move in a linear motion immediately prior to reaching an extended position; and
- coupling movement of the pinion to the lance holder such that the lance holder is extended when the pinion reaches a predetermined position on the predetermined path.

Alternative Process HH

The method of Alternative Process GG comprising stopping movement of the pinion when the pinion reaches the predetermined position.

Alternative Process II

The method of Alternative Process GG comprising temporarily preventing the pinion from rotating when the pinion reaches the predetermined position.

Alternative Process JJ

The method of Alternative Process GG comprising guiding a frame comprising the predetermined path along a predefined track.

Alternative Process KK

A method of creating a laceration with a lance, the method comprising:
- moving a pinion along a predetermined path;
- coupling movement of a lance holder to movement of the pinion; and
- preventing the lance holder from extending beyond a predetermined depth.

Alternative Process LL

The method of Alternative Process KK comprising:
- retracting the lance holder from the predetermined depth; and
- rotating the pinion in a single rotational direction, wherein rotating the pinion causes the lance holder to sequentially extend and retract.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the claimed invention, which is set forth in the following claims.

What is claimed is:

1. A method of using a lancing device, the method comprising the acts of:
    providing a lancing device including a parallelogram-shaped gear rack, the gear rack comprising teeth, a pinion rotatably supported in the gear rack, a slider-crank system including a drive arm coupled to the pinion, a lance holder coupled to the drive arm, and a drive spring coupled to the gear rack;

moving the gear rack via the drive spring;

rotating the pinion in response to the movement of the gear rack; and driving the lance holder in linear motion via the slider-crank system in response to the rotation of the pinion.

2. The method of claim 1 wherein the coupling of the drive arm to the pinion includes a drive wheel.

3. The method of claim 1 wherein the parallelogram-shaped gear rack comprises a proximal acute angle, and a distal acute angle positioned closer to the lance holder than the proximal acute angle, and wherein the pinion rotates 180° when moving between the distal acute angle and the proximal acute angle.

4. The method of claim 3 wherein the lance holder moves from a cocked position to a fired position and wherein the lance holder is in the cocked position when the pinion is positioned at the distal acute angle and in the fired position when the pinion is positioned at the proximal acute angle.

5. The method of claim 3 wherein the lancing device further comprises a first guide pin fixed relative to the parallelogram-shaped gear rack and a first guide track linearly fixed relative to the pinion, the first guide pin interfacing with the first guide track as the parallelogram-shaped gear rack moves relative to the pinion, whereby movement of the rack is guided.

6. The method of claim 5 wherein the lancing device further comprises:

a second guide pin fixed relative to the parallelogram-shaped gear rack, the gear rack being positioned between the first and second guide pins; and a second guide track fixed relative to the first guide track, wherein the pinion is positioned between the first and second guide tracks and the second guide pin interfaces with the second guide track as the parallelogram-shaped gear rack moves relative to the pinion.

7. The method of claim 6 wherein the first and second guide tracks are parallelogram shaped.

8. The method of claim 5 wherein the first guide track is parallelogram shaped.

9. The method of claim 8 wherein the first guide pin is cylindrically shaped.

10. The method of claim 1 wherein the parallelogram-shaped gear rack is positioned between the lance holder and the drive spring.

11. The method of claim 1 wherein the parallelogram-shaped gear rack comprises four segments, wherein the rotation of the pinion is between a first acute angle position and a second acute angle position, the pinion comprising pinion teeth and wherein the rack segments comprise rack teeth being adapted to engage the pinion teeth and at least two rack teeth on each segment are modified to reduce chances of the pinion jamming at either one of the first and second acute angle positions.

12. The method of claim 1, wherein the pinion rotates 360° as the lance holder linearly moves from a cocked position to a fired position and back to the cocked position.

13. The method of claim 1, wherein the lance holder moves from the cocked position to the fired position and back to the cocked position as the pinion rotates 360°.

14. A method of using a lancing device, the method comprising the acts of:

providing a frame including a parallelogram-shaped gear rack, the gear rack comprising teeth, a pinion rotatably mounted to interface the gear rack, a lance holder, and a drive spring coupled to the gear rack, the frame being movably supported;

moving the gear rack via the drive spring;

rotating the pinion in response to the movement of the gear rack; and moving the lance holder between a fired position and a cocked position, wherein movement of the lance holder is in response to rotation of the pinion.

15. The method of claim 14, wherein the lance holder moves from the cocked position to the fired position as the pinion rotates 180°.

16. The method of claim 15 wherein the pinion traverses approximately one-half of the rack as the lance holder moves from the cocked position to the fired position.

17. The method of claim 15 wherein the parallelogram-shaped rack comprises a first acute angle and a second acute angle and the pinion is positioned proximate to the first acute angle when the lance holder is in the cocked position and the pinion is positioned proximate to the second acute angle when the lance holder is in the fired position.

18. The method of claim 17, wherein the pinion rotates 180° as the pinion moves from the first acute angle to the second acute angle.

19. The method of claim 14, wherein the lance holder moves from the cocked position to the fired position and back to the cocked position as the pinion rotates 360°.

* * * * *